United States Patent [19]

Baker, Sr. et al.

[11] Patent Number: 4,662,516
[45] Date of Patent: May 5, 1987

[54] SYRINGE DISPOSAL TECHNIQUES

[76] Inventors: Richard E. Baker, Sr.; Richard E. Baker, Jr., both of 2610 Croddy Way, Unit D, Santa Ana, Calif. 92704

[21] Appl. No.: 836,725

[22] Filed: Mar. 6, 1986

[51] Int. Cl.⁴ .................. A61M 5/32; B65D 83/10
[52] U.S. Cl. ............................ 206/363; 206/366; 206/370
[58] Field of Search .......... 206/366, 363, 370, 380, 206/63.8, 381, 216

[56] References Cited

U.S. PATENT DOCUMENTS

| | | | |
|---|---|---|---|
| 3,527,192 | 9/1970 | Ferrara | 220/404 |
| 3,762,599 | 10/1973 | Bourgeois | 220/403 |
| 4,121,755 | 10/1978 | Meseke et al. | 206/366 |
| 4,485,918 | 12/1984 | Mayer | 206/366 |
| 4,494,652 | 1/1985 | Nelson et al. | 206/366 |
| 4,576,281 | 3/1986 | Kirksey | 206/366 |

Primary Examiner—Joseph Man-Fu Moy
Attorney, Agent, or Firm—I. Michael Bak-Boychuk

[57] ABSTRACT

A series of wall units are provided, each including a pivoted, lockable panel and each including an upper opening in which the edges of a basket supporting the top surface of a thermoplastic liner. This top surface includes a convolved opening through which medical debris is collected onto a thick thermoplastic bottom insert, the liner being periodically removed from the basket and heated in the course of sterilization to melt the top and bottom surfaces around the debris.

2 Claims, 5 Drawing Figures

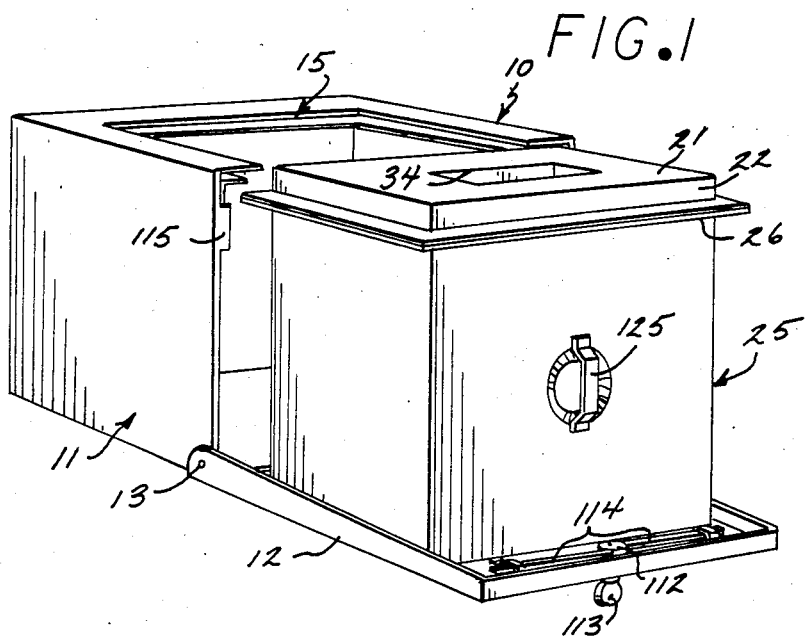
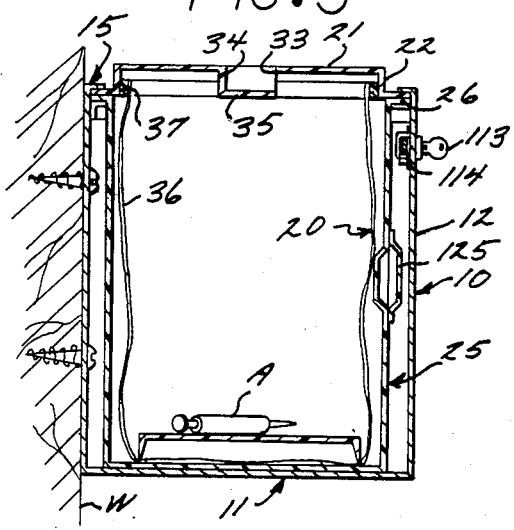
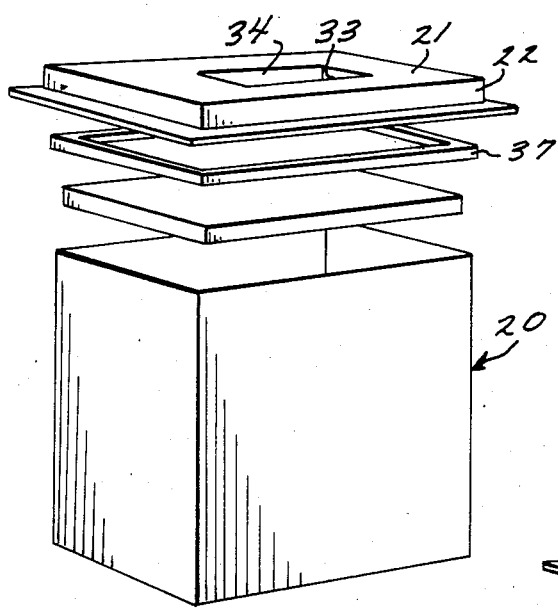
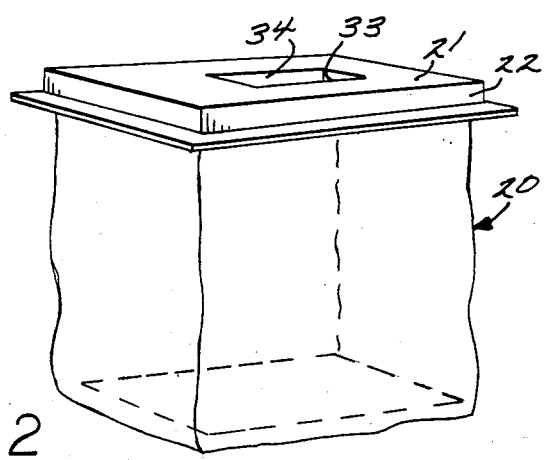

SYRINGE DISPOSAL TECHNIQUES

BACKGROUND OF THE INVENTION

1. Field of the Invention

The present invention relates to syringe disposal systems, and more particularly to syringe disposal receptacles conformed for encapsulation prior to discarding.

2. Description of the Prior Art

In our prior U.S. Pat. No. Des. 264,879 we have disclosed a wall mounted syringe receptacle for use in hospitals and other facilities. Since that time we have discovered improvements in the structure of such receptacles, improvements which render such particularly suitable for encapsulation subsequent to use.

In any medical facility the disposal of contaminated syringes and other medical devices is a problem of profound concern. The interests of protecting the general populace from the spread of certain virulent disease strains has led to the practice in most medical facilities where any utensils exposed thereto are to be discarded after use. One utensil of prevalent use is the syringe by which various medications are introduced into the body of a patient. Syringes, however, in today's culture, also have secondary functions for those bent on introducing illicit drugs into their person. Thus, there are two concerns in any disposal procedure, i.e., the clinical concern for limiting unwanted contamination and spread of disease and the concern over unauthorized use of medical devices.

One should note that today's disease patterns occasionally encounter virulent strains which sometimes are not adequately resolved by conventional sterilization. Thus, the process of sterilization is often made in tandem with procedures by which the contaminated utensil is destroyed and encapsulated to preclude its subsequent reuse. It is these exact features that are addressed by the present invention in a disposal procedure which both encapsulates the discarded device and is also convenient in use.

SUMMARY OF THE INVENTION

Accordingly, it is the general purpose and object of the present invention to provide a wall mounted receptacle comprising an exterior lockable housing into which plastic inserts may be received, each plastic insert being conformed to include an upper, tortuous path secured to a plastic bag for encapsulation of the discarded utensils in the course of sterilizing.

Other objects of the invention are to provide a convenient receptacle for storing and discarding medical utensils.

Yet additional objects of the invention are to provide a disposable receptacle which can be conveniently mounted on the walls of a hospital.

Briefly, these and other objects are accomplished within the present invention by providing an exterior, rigid, lockable housing which may be secured to the walls of a medical facility, the housing including an upper opening conformed to engage the top surface of a plastic insert conformed to receive medical utensils therethrough. More specifically, the upper portion of the insert may be formed as a rectangular surface having a peripheral edge bead receivable in an edge groove of the wall mounted housing and having a collapsable bag or container depending from the edge for containing discarded utensils therein.

The upper rigid surface, moreover, may include a slot provided with a downwardly dependent lip to form a tortuous path for any receptacles discarded therein, the rigid surface and the bag deployed therefrom being both formed of a thermoplastic material. At the same time, a thermoplastic, rigid bottom panel may be inserted in the bag, both the top and bottom panels providing the thermoplastic mass for encapsulation. Thus any utensils collected in this insertable receptacle, once exposed to heat, will be encapsulated by this material, forming a rigid, contiguous mass from which removal is either difficult or virtually impossible to achieve. In this form the conglomerated combination of the insert and the utensils may be carried away for disposal or may be transported for incineration.

Thus, a convenient technique for disposing used medical utensils is provided, a technique which also renders the collection thereof convenient and inexpensive.

BRIEF DESCRIPTION OF THE DRAWINGS

FIG. 1 is a perspective illustration of a disposal arrangement constructed in accordance with the present invention;

FIG. 2 is a perspective illustration of a thermo plastic liner useful with the present invention;

FIG. 3 is a sectional side view of the arrangement shown in FIG. 1, illustrated in its closed position;

FIG. 4 is a perspective illustration, separated by parts, of the liner shown in FIG. 2; and FIG. 5 is a sectional view of a molten conglomerate including the structure of said liner.

DESCRIPTION OF THE SPECIFIC EMBODIMENT

As shown in FIGS. 1 through 4 the inventive disposal system, generally designated by the numeral 10, comprises an exterior housing 11 of substantially rectangular construction, housing 11 including a front panel 12 hinged for outward deployment from a pivotal hinge 13 approximate the lower edge thereof. Panel 12, when closed, completes the periphery of a rectangular upper opening 15, and when open permits the removal of articles retained in the housing. In this form-housing 11 may be secured to any wall surface W of a medical facility, the front face plate 12 being locked thereto to form an enclosure. Dimensionally, housing 11, together with the front panel 12, define an interior cavity conformed to receive a removeable basket 25, once again, open at the top and bounded thereat by an outward peripheral edge 26. This basket 25 supports in suspension on edge 26, a thermoplastic bag or liner 20.

To complete the closure the upper opening 15 is provided with a peripheral recess 17 conformed to receive an edge bead 18 formed around an upper panel 21 of an insertable plastic container 20. This upper panel 21 is once again of rectangular plan form including a raised section 22 in which a slot 23 is formed. This slot 23 includes a downwardly directed edge piece 24 from which a cantelevered lip 35 extends below the slot opening.

Thus, a tortuous path is formed through which articles like syringes may be passed but which precludes the insertion of a hand for the removal, panel 21 upon insertion into groove 17 forming the upper closure. Panel 21 is attached to a plastic, bag-like liner 36 retained by an edge piece 37 within the enlargement 22. Moreover, liner 36 may include a rectangular, plastic insert 38 of substantial thickness at the bottom thereof.

Accordingly, articles collected in bag 36 between the cover 21 and the bottom piece 38 can then be taken out periodically and placed in an autoclave for sterilization. In the course of the sterilization both the upper and the lower panels of the liner melt and encapsulate any articles A collected therebetween in a conglomerated mass of molten plastic. This molten mass, as shown in FIG. 5, may then be transported for burial or may be placed in an incinerator for further destruction.

One should note that the foregoing liner assembly 20 entails only two substantive plastic masses, i.e., the top cover 21 and the bottom piece 38. Thus, the expense of encapsulation is limited to those two pieces, the remainder of the liner, i.e, the bag 36, being a conventional purchased item fixed to the top and bottom pieces by well-known processes of local melting. To achieve this attachment, bag 36 may be wrapped around the edge piece 37 which is then fixed within the interior of the top cover 21 and the bottom piece 38 may be provided with a peripheral edge strip 38a which, once again, may be fixed to the bag by crimping or spot melting.

Thus, only two molded pieces of any substance are required, each of conventional thermoplastic structure and each conveniently replicated with minimal cost. Moreover, convenience in insertion and replacement is achieved by the basket 25 conformed for receiving said liner with the edge of the top cover resting on the upper edge thereof. This basket can then be inserted by sliding on panel 12 into the interior of housing 11 thereby forming a further barrier against inadvertent puncture or tearing. Once inserted within groove 17 basket 25, together with the top panel 21 resting thereon, are locked in place by a lock mechanism 112 on panel 12, mechanism 112 being articulated by a key 113 to extend arms 114 into engagement against tabs 115 formed on the vertical edges of housing 11. The debris collected in the liner can then be periodically collected by unlocking panel 12 and withdrawing the basket 25 through the use of a handle 125. Basket 25 can thus be periodically sterilized along with other sterilized equipment, having first removed therefrom the debris encapsulating liner.

Obviously many modifications and changes may be made to the foregoing without departing from the spirit of the invention. It is therefore intended that the scope of the invention be determined solely on the claims appended hereto.

What is claimed is:

1. A medical article collection assembly comprising:
   a substantially rectangular housing including a front panel pivoted from a lower edge thereof and an upper substantially rectangular opening defined by the upper interiorly directed edges of said housing and said front panel;
   a basket conformed for insertion into said housing in alignment subjacent said edges defining said upper opening;
   a thermoplastic liner receivable in said basket and including a top surface engageable between said basket and said upper opening, said top surface being provided with a tortuous path for insertion of said medical articles in the form of a slot provided with a downwardly directed edge having a cantelevered surface piece extending subjacent said slot in spaced relationship relative thereto to extend over the substantial dimension of said slot;
   said liner including a bottom surface of thermoplastic material;
   said top and bottom surfaces include sufficient thermoplastic mass to enclose said articles by melting.

2. Apparatus in accordance with claim 1 wherein:
   said front panel is provided with locking mechanism for engagement thereof to said housing.

* * * * *